United States Patent [19]

Neidleman et al.

[11] 4,247,641
[45] Jan. 27, 1981

[54] METHOD FOR PRODUCING EPOXIDES AND GLYCOLS FROM ALKENES

[75] Inventors: Saul L. Neidleman, Oakland; William F. Amon, Jr., Danville; John Geigert, Concord, all of Calif.

[73] Assignee: Cetus Corporation, Berkeley, Calif.

[21] Appl. No.: 42,219

[22] Filed: May 29, 1979

Related U.S. Application Data

[63] Continuation-in-part of Ser. No. 940,638, Sep. 8, 1978, abandoned.

[51] Int. Cl.³ .............................................. C12P 17/02
[52] U.S. Cl. .................................. 435/123; 435/157; 435/232
[58] Field of Search ....................... 435/52, 53, 55, 58, 435/123, 59, 158, 157, 132, 232

[56] References Cited

U.S. PATENT DOCUMENTS

| | | | |
|---|---|---|---|
| 3,110,733 | 11/1963 | Weisenborn et al. | 435/58 X |
| 3,162,655 | 12/1964 | Bagli | 435/55 X |
| 3,198,809 | 8/1965 | Nielson et al. | 435/53 X |
| 3,520,779 | 7/1970 | Levine et al. | 435/52 X |
| 3,527,673 | 9/1970 | Neidleman et al. | 435/52 X |
| 3,528,886 | 9/1970 | Niedleman et al. | 435/53 |
| 4,106,986 | 8/1978 | Suzuki et al. | 435/123 |

*Primary Examiner*—Robert A. Yoncoskie
*Attorney, Agent, or Firm*—Fitch, Even, Tabin, Flannery & Welsh

[57] ABSTRACT

A method is described for the manufacture of epoxides or glycols from olefins. An olefin is contacted with a reaction mixture of a halogenating enzyme, an oxydizing agent and a halide ion source, for a sufficient period to convert the olefin to a halohydrin. The halohydrin is then converted to an epoxide or glycol.

31 Claims, No Drawings

METHOD FOR PRODUCING EPOXIDES AND GLYCOLS FROM ALKENES

This application is a continuation-in-part of application Ser. No. 940,638 filed Sept. 8, 1978, now abandoned.

This invention relates generally to an enzymatic process for making useful commercial products from alkenes. More particularly, the invention relates to an improved process for the production of epoxides and glycols from alkenes wherein an enzyme is used to produce an intermediate halohydrin and the halohydrin is converted to an epoxide or glycol by an enzymatic or chemical process.

As used herein, the term "alkene" is intended to include any open chain hydrocarbon having carbon to carbon double bonds, wherein each of the carbons containing at least one of the double bonds is joined to either hydrogen or another carbon. Alkenes include compounds having more than one double bond. The term "olefin" as used herein is intended to have the same meaning as "alkene".

A number of useful chemical products, e.g. surfactants, humectants, polymers and plasticizers, are produced from alkenes such as ethylene and propylene. Examples of such useful products prepared from alkenes include epoxides and glycols. The preparation of other products often involves first producing an epoxide or glycol and then reacting it in some subsequent chemical process to form the desired compound. To form the epoxide two general approaches have been used traditionally. The first of these is to oxidize the alkene directly. The second is to form an intermediate halohydrin and then convert it with a base to form the epoxide. Glycols usually are produced by hydrating the corresponding epoxide. In recent years the development of alternate processes for producing epoxides and glycols has been receiving considerable attention, due to the high commercial value of such materials, the extensive energy requirements of the known processes and the high cost of required reaction materials.

Processes utilizing direct oxidation, currently a commercially favored path from ethylene to ethylene oxide, normally require pure oxygen and supported silver oxide catalyst, both of which add to cost and necessitate expensive safety procedures and devices. Moreover, the elevated temperature required in the process, typically 270° C., increases the energy cost in the process. Also, reaction yields are decreased by the production of substantial quantities of carbon dioxide and water as by-products.

Processes involving the production of epoxides by conversion of an intermediate halohydrin, currently a commercially favored path from propylene to propylene oxide, have encountered problems in the formation of the halohydrin itself. Known processes for the production of halohydrins from alkenes typically involve the addition of alkene, halogen and water in a reactor under controlled conditions. Such processes frequently result in the production of undesirable side products such as hydrochloric acid (which requires neutralization), haloalkanes and bis- (haloalkyl) ethers. Moreover, use of free halogen in any process requires expensive control procedures and equipment to prevent loss of this toxic reactant. Also, the use of free halogen is now preferably avoided because of the energy-intensive process employed for its production.

It is a principal object of the present invention to provide an improved process for producing epoxides and glycols from alkenes.

Another object of the invention is to provide a process for producing epoxides and glycols from alkenes wherein an intermediate halohydrin is produced without requiring the use of free halogen.

A further object of the invention is to provide a process for the production of epoxides and glycols from alkenes which is relatively safe, low in cost, and low in energy requirements as compared with known processes.

It is a still further object of the present invention to provide a general process for the conversion of a large number of different alkenes to the epoxide or glycol through a halohydrin intermediate under conditions wherein the necessity for halohydrin isolation is avoided.

Other objects of the present invention will become more apparent from the following detailed description and accompanying claims. In the description and claims, all proportions and percentages are by weight, all pressures are standard atmospheric, and all temperatures are in degrees centigrade, unless otherwise specified.

In general, in accordance with one aspect of the present invention, the halohydrin of an olefin is produced by introducing the olefin into a reaction mixture of a halogenating enzyme, a source of halide ion, and an oxidizing agent. The reaction of the olefin to provide the halohydrin of the olefin proceeds spontaneously and rapidly under ambient conditions of temperature and pressure. The halohydrin is then converted to the epoxide or glycol by an enzymatic or chemical process.

As used herein, the term "epoxide" includes oxides and the term "glycol" is the same as diol where in the hydroxyl groups are on adjacent carbons.

The enzymatic halogenating process of the present invention has several advantages over the present state of the art for producing halohydrins from olefins, including the following: The use of inexpensive, less dangerous, inorganic halide, rather than elemental halogen, i.e. bromide ion rather than bromine; use of ambient temperature; and use of standard or close to standard atmospheric pressure.

In addition to proceeding favorably at room temperature, this enzymatic process involves the use of dilute $H_2O_2$, not necessarily purified. The $H_2O_2$ may be added directly or generated in situ by an enzymatic or chemical reaction. This reduces the cost of the $H_2O_2$ as compared to the cost of concentrated, purified material; increases the safe usage of the substance; and extends the life of the halogenating enzyme. The in situ generation of peroxide will be discussed below.

The olefins useful in the process can be broadly defined as any hydrocarbon containing a carbon to carbon double bond, represented by the following structural formula:

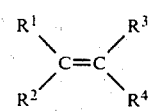

wherein each of $R_1$, $R_2$, $R_3$ and $R_4$ is selected from a group consisting of:

(1) hydrogen
(2) a straight chain
(3) a branched chain
(4) a cyclic
} saturated or unsaturated hydrocarbon radical having from 1 to 12 carbon atoms;

and provided that all direct linkages to the carbons of the double bond are either hydrogen or carbon, that none of the R groups are themselves connected such as to form a cyclic ring and that no carbons adjacent to the carbons of the double bond are carbonyl.

Representative olefins are:

| Olefin | $R^1$ | $R^2$ | $R^3$ | $R^4$ |
|---|---|---|---|---|
| ethylene | H | H | H | H |
| propylene | $CH_3$ | H | H | H |
| butene-1 | $C_2H_5$ | H | H | H |
| pentene-1 | $C_3H_7$ | H | H | H |
| octene-1 | $C_6H_{13}$ | H | H | H |
| decene-1 | $C_8H_{17}$ | H | H | H |
| dodecene-1 | $C_{10}H_{21}$ | H | H | H |
| isobutylene | $CH_3$ | $CH_3$ | H | H |
| cis-butene-2 | $CH_3$ | H | $CH_3$ | H |
| trans-butene-2 | $CH_3$ | H | H | $CH_3$ |
| 2-methyl-butene-2 | $CH_3$ | $CH_3$ | $CH_3$ | H |
| 1,3-butadiene | $CH_2=CH$ | H | H | H |
| 1,4-pentadiene | $H_2C=CHCH_2$ | H | H | H |
| isoprene | $H_2C=C(CH_3)$ | H | H | H |
| 1,7-octadiene | $H_2C=CH(CH_2)_4$ | H | H | H |

The broad definition of open-chain olefins includes olefins where $R^1$, $R^2$, $R^3$, and/or $R^4$ can be an aromatic or heteroatom-containing group, provided that the substituents are inert to the prescribed reaction condition, or do not deactivate the normally reactive carbon to carbon double bond susceptible to halohydrin formation and further provided that the conditions previously set forth for the selection of $R^1$, $R^2$, $R^3$ and $R^4$ are observed.

Representative olefins containing such aromatic or heteroatom groups are:

| Olefin | $R^1$ | $R^2$ | $R^3$ | $R^4$ |
|---|---|---|---|---|
| styrene | $C_6H_5$ | H | H | H |
| allyl alcohol | $HOCH_2$ | H | H | H |
| allyl chloride | $ClCH_2$ | H | H | H |
| allyl bromide | $BrCH_2$ | H | H | H |

The broad definition of olefins also includes olefins containing cumulated double bonds, such as allene:

$$CH_2=C=CH_2$$

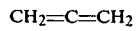

The present invention makes use of certain peroxidases which have catalytic activity with respect to breaking the double bond of olefin compounds and promoting hydroxylation on one of the carbons while promoting halogenation on the adjacent carbon under particular reaction conditions. The peroxidase enzymes capable of providing catalytic activity as described herein are referred to as "halogenating enzymes".

A preferred halogenating enzyme is derived from the microorganism *Caldariomyces fumago*. Other sources of halogenating enzyme include seaweed, milk (lactoperoxidase), thyroid (thyroid peroxidase), leukocytes (myeloperoxidase) and horseradish (horseradish peroxidase). Certain of these peroxidases are commercially available.

For ease of discussion, various aspects of the present invention will be described with particularity, but not exclusively, in connection with use of the preferred peroxidase, chloroperoxidase, derived from *Caldariomyces fumago*. The microorganism, *Caldariomyces fumago*, may be grown as a static or agitated, submerged culture in Czapek-Dox medium at room temperature for 3 to 10 days by conventional methods. The halogenating enzyme, chloroperoxidase, is prepared from an aqueous homogenate of the mycelial pads of the microorganism grown under static conditions or from the filtrate of the microorganism grown under static or agitated submerged culture conditions.

The halogenating enzyme may also be used in an immobilized form. Processes for enzyme immobilization are familiar to those skilled in the art, and include reacting either a solution of the enzyme or a suspension of enzyme containing cells with one of a broad range of organic and inorganic supports. Included among these are polyacrylamide, ethylene-maleic acid copolymers, methacrylic-based polymers, polypeptides, styrene-based polymers, agarose, cellulose, dextran, porous glass beads, and aluminum or titanium hydroxide. Enzymes in this form have increased stability, extended life and usefulness, and recoverability. Reactions employing immobilized enzymes may be run in columns or reaction tanks.

In addition to the halogenating enzyme, a source of inorganic halide and an oxidizing agent are required in the reaction mixture. A preferred oxidizing agent is hydrogen peroxide, which may be added directly to the mixture in a single batch addition, or in a continuous slow feed. It may alternatively be generated as a slow feed in situ by the use of a hydrogen peroxide-producing enzyme system. Such enzyme systems are well known in the art, and include glucose oxidase in the presence of glucose, D- and L-amino acid oxidases in the presence of D- and L-methionine, methanol oxidase in the presence of methanol, and diamine oxidases in the presence of histamine. The hydrogen peroxide-generating system may be present in the non-immobilized or immobilized state as with the halogenating enzyme. The hydrogen peroxide may also be generated by a chemical reaction, such as the anthraquinone or isopropyl alcohol oxidation processes.

With in situ generation of hydrogen peroxide using glucose oxidase or methanol oxidase, coproducts include gluconic acid (in the case of glucose oxidase) and formaldehyde (in the case of methanol oxidase). Although each of these coproducts is commercially useful, it is conceivable that if the method of the invention is adopted on a large scale for the production of epoxides and glycols, the amount of coproduct produced by in situ hydrogen peroxide generation could exceed market demand by a substantial amount. Under such circumstances, two possibilities are presented. The first is to find additional uses and therefore additional markets for the coproducts gluconic acid or formaldehyde. The other possibility, however, is to develop or modify the process in such a way as to produce a coproduct which is capable of being absorbed by relatively higher market demand.

It may therefore be preferable that the enzyme used for the production of hydrogen peroxide in situ be glucose-2-oxidase. Using glucose as a substrate, glucose-2-oxidase catalyzes the following reaction (Volc et al, *Folia Microbiol.* 23:292–298, 1978):

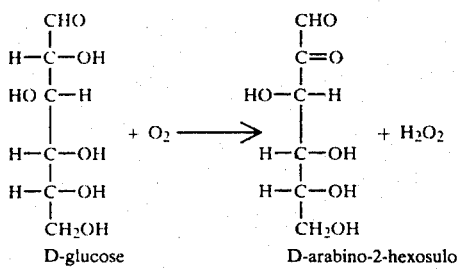

D-glucose → D-arabino-2-hexosulose

The D-arabino-2-hexosulose thus produced may be readily converted to D-fructose by simple chemical hydrogenation as follows:

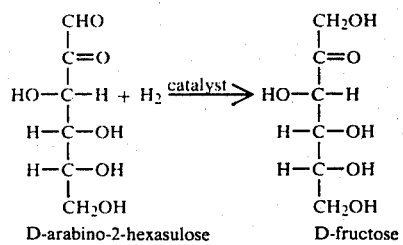

D-arabino-2-hexasulose → D-fructose

The advantage of relatively low-cost coproduction of D-fructose is the high desirability of fructose as a sweetener. The substantially higher sweetness of fructose per calorie or unit weight as compared with dextrose or sucrose offers distinct advantages for a wide variety of food applications. The current price and restricted availability of fructose, however, has limited its use. The present invention would be capable of generating large quantities of fructose at prices competitive with sucrose as currently provided.

The hydrogen peroxide is present preferably in a molar ratio of from about 0.5:1 to about 50:1, most preferably in a ratio of about 1:1 or less with respect to the olefin. The molar ratio preferences refer to the average presence of hydrogen peroxide during the reaction. The actual molar ratio will usually vary during the reaction and the molar ratio at any particular time may be above or below the ranges cited. Other suitable oxidizing agents include organic peroxides, such as methyl, ethyl, or butyl peroxides.

The halogen source may be any of the water-soluble halide salts. The preferred halogen sources are the chloride, bromide, and iodide salts of the alkali metals, sodium and potassium. The salts are present in the reaction mixture at a level sufficient to provide a slight excess of halide ion with respect to the stoichiometric amount required for the reaction.

The reaction is conducted within the pH range of from about 2.2 to about 8.0. The pH of the reaction may be maintained within the desired range by use of a buffering agent. Suitable buffers include sodium or potassium phosphate, gluconate, citrate, formate, and acetate based systems. Other suitable techniques besides buffering may be used for pH control and adjustment. The reaction is preferably conducted in an aqueous medium. While some of the olefins that can be converted by the process are substantially insoluble in an aqueous medium, the reaction, nevertheless, occurs satisfactorily under conditions of mixing, or other modes of dispersion, which provide sufficient substrate solubility for the reaction.

It is also contemplated that the reaction can be conducted in the presence of low levels of organic solvents, such as lower aliphatic alcohols, ketones, dioxane, or dimethylformamide to increase substrate solubility. The reaction is preferably conducted under aerobic conditions and in the temperature range of 15° to about 50°, preferably about 20° to about 30°.

A resulting intermediate product in the method of the present invention is a halohydrin represented by the following structure:

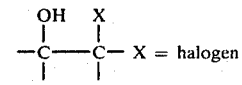

The halogen is predominantly attached to the carbon atom that yields the least stable carbonium ion. Thus, from monoolefinic hydrocarbons such as 1-olefins, there is obtained 1-halo-2-hydroxy hydrocarbons (major) and 2-halo-1-hydroxy hydrocarbons (minor):

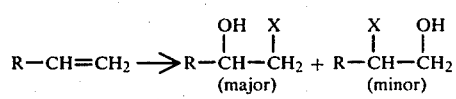

From polyolefinic hydrocarbons, there may be obtained both monohalohydrins and polyhalohydrins, as in the case of 1,3-butadiene:

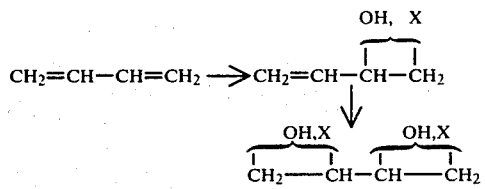

From olefins containing cumulative double bonds, there may be obtained both monohalohydrins and polyhalohydrins, as in the case of allene:

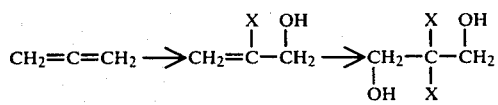

The components other than the olefin, namely the halogenating enzyme, the oxidizing agent, the halide ion source and the buffer agent, are simply mixed together in water or mixed aqueous and organic media to provide a reaction mixture.

The halohydrins formed by the reaction are easily converted to the oxide, which may itself be useful or which may be converted to a glycol or other useful derivative of the olefin in accordance with conventional procedures. To convert the halohydrin to an epoxide, any of several techniques may be employed. For example, the halohydrin may be converted to the epoxide by contacting with an aqueous slurry of slaked lime. Hydration of the epoxide results in the glycol.

In a preferred embodiment of the present invention, the conversion of the halohydrin to an epoxide is effected by means of an epoxidase used either in a free or immobilized form. One such enzyme is the halohydrin epoxidase of Flavobacterium sp. cells. Similar activity has been detected in a variety of other organisms such as the fungus *Caldariomyces fumago* and the seaweed

*Laurencia pacifica*. The enzyme carries out the following reaction:

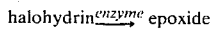

Specifically for propylene bromohydrin:

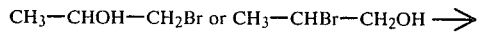

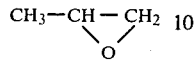

For this embodiment, the steps of the method of the invention for the production of an epoxide from an alkene may be carried out sequentially. In a most preferred embodiment the steps are carried out simultaneously in the same reactor and the alkene is converted directly to the epoxide solely through use of enzymes without recovery or isolation of a halohydrin intermediate.

As previously indicated, the components of the reaction mixture, namely the olefin, the halogenating enzyme, the oxidizing agent, the halide ion source, and the buffering agent are simply mixed together in water or mixed aqueous or organic media, and agitated for a period of from about 30 seconds to about 1 hour to obtain the halohydrin. Lower linear olefins, such as ethylene or propylene, which are gaseous, can be reacted upon by simply passing the gaseous olefins through the reaction mixture. Equally important and of commercial significance is the discovery that (1) the same equipment can be used regardless of the specific nature of the alkene, and (2) mixed alkene substrates can be simultaneously converted to their respective halohydrins. Mixtures of alkenes can provide increased total solubility of the alkenes in water (and thus increased conversion rate) and can improve productivity of the enzyme system. Of commercial significance also is the ability to use crude substrates or substrate mixtures, thus reducing the cost of raw materials. The intentional inclusion of small controlled amounts of a given alkene into the larger stream of another enables the economic production of a low-volume specialty product. Thus, for example, the halohydrins or oxygenated derivatives of butadiene could be co-produced with propylene halohydrin, epoxide or glycol in a propylene predominant system.

The following examples illustrate various features of the invention, but are in no way intended to limit the scope of the invention which is defined in the appended claims. In many of the examples, preparation of only the intermediate halohydrins is discussed, since conversion of the halohydrin to the epoxide can be achieved in all cases by suitable procedures such as alkaline or enzymatic treatment.

EXAMPLES 1–18

Gaseous Olefins

Dilute hydrogen peroxide (1 mg/ml final), halide salt (10 mg/ml final) and 0.1 M potassium phosphate buffer are mixed together in a 100 milliliter Pyrex flask at room temperature and room pressure. The halogenating enzyme is added and the gaseous olefin is bubbled into the reaction mixture. Sample is withdrawn at 30 minutes and analyzed for halohydrin.

The halogenating enzymes are prepared as follows:

Chloroperoxidase (CP). Mycelial pads of *Caldariomyces fumago* (ATCC 16373) are grown on potato agar slants as follows: Sliced potato (200 g) is cooked in distilled water (500 ml) for 40 minutes and then strained. A solution of glucose (21 g) and agar (20 g) in distilled water (500 ml) is added to the strained solution. The pH is adjusted to 6.8 and the volume is brought to 1 liter with distilled water. The medium is sterilized at 121° for 15 minutes. The organism is inoculated on the potato agar slants, produced in accordance with the above procedure, and is grown for about one week at room temperature. The organism is then used to inoculate the soybean-glucose medium (50 ml) prepared as follows: to 1 liter of distilled water are added extraction process soybean meal (30 g), glucose (30 g), and $CaCO_3$ (7 g). The medium is sterilized at 121° for 30 minutes and is then inoculated with the organism after cooling. The organism is grown for 4–5 days on a rotary shaker at 25°. 5 ml of this material is used to inoculate a 500 ml Erlenmeyer flask containing 100 ml of a modified Czepek-Dox medium prepared by adding the following to 1 liter of distilled water: $NaNO_3$ (3 g), $KH_2PO_4$ (1 g), KCl (0.5 g), $MgSO_4 \cdot 7H_2O$ (10 mg) and glucose (40 g). The medium is sterilized at 121° for 20 minutes prior to inoculation with the organism. The organism is grown under static conditions at room temperature 5–7 days. The black mycelial pads which form are collected, rinsed with distilled water, and stored in plastic bags in a freezer at −10° for subsequent use.

The halogenating enzyme is prepared by grinding 6 mycelial pads (prepared in accordance with the above procedures) with 60 g acid-washed sand and 60 ml distilled water for 2 minutes in a Virtis 45 homogenizer. The homogenate is centrifuged while cold and the supernatant solution filtered through Whatman #1 paper at room temperature. The filtrate is concentrated about 10-fold using a rotary film evaporator at reduced pressure and temperature less than 35°. The concentrate is chilled at 0° in an ice bath, and prechilled (0°) ethanol is added until 45% ethanol (v/v) is reached. The mixture is stirred vigorously for 15 minutes, and then centrifuged at −10° (at 15,000 g) with a 55–34 rotor in a Sorval RC-5 Superspeed for 15 minutes. The black sediment is discarded. To the centrifugate, cooled at 0°, is added additional prechilled ethanol to give 65% ethanol (v/v). The mixture is slowly stirred for 30 minutes at 0°, and then centrifuged as before. The centrifugate is discarded and the precipitate containing the chloroperoxidase activity is dissolved in a minimum volume of 0.05 M potassium buffer (pH 7). The enzyme solution is stored at −20°. The activity is measured as 80 monochlorodimedon units/ml. (Ref: Morris, D. R. and Hager, L. P., *J. Biol. Chem.* 241, 1763 (1966)).

Lactoperoxidase (LP). Purchased from Sigma Chemical Company (Catalogue #L-7129).

Seaweed Peroxidase[1] (SWP[1]). *Laurencia pacifica* obtained along the coast of La Jolla, California, is prepared by grinding and dispersing 5 g of the seaweed in 10 ml of 0.3 M potassium phosphate buffer (pH 6.0) for 2 minutes in a Virtis 45 homogenizer.

Seaweed Peroxidase[2] (SWP[2]). Coralina sp. obtained along the coast of La Jolla, California is ground in a Virtis 45 homogenizer for 5 minutes in distilled water. The homogenate is spun at 20,000 rpm for 20 minutes. The supernatant is decanted and saved. The pellet is resuspended in distilled water and recentrifuged. This supernatant and previous supernatant are combined. The solution is brought first to 33%, then to 55% saturation in ammonium sulfate. Centrifugation and separation of pellet is performed at each step. The 33%–55% pellet fraction is passed through a DEAE column using a 0.3 M to 1 M phosphate buffer (pH 6.0) gradient. The fraction which elutes at 1 M is dialyzed against 20 mM phosphate buffer (pH 6) overnight. This preparation is stored at −20° until needed. The activity is measured as tion time (2 minutes) and identical mass spectra (M+; m/e 58).

Variable conditions and results are set forth in Table I.

The reactions are found clean, i.e., no detected halogenated byproduct formation.

TABLE I

| Ex. | Olefin | Halide | Enzyme | (Units) | pH | Halohydrin Produced | (mg/ml) |
|---|---|---|---|---|---|---|---|
| 1 | Ethylene | KCl | CP | (10) | 3 | 2-chloroethanol | (0.1) |
| 2 | Ethylene | KBr | CP | (10) | 3 | 2-bromoethanol | (1.8) |
| 3 | Ethylene | KBr | LP | (50) | 6 | 2-bromoethanol | (0.5) |
| 4 | Propylene | KCl | CP | (10) | 3 | 1-chloro-2-propanol + 2-chloro-1-propanol (90:10) | (0.1) |
| 5 | Propylene | KCl | LP | (50) | 6 | 1-chloro-2-propanol + 2-chloro-1-propanol (90:10) | (0.3) |
| 6 | Propylene | KBr | CP | (10) | 3 | 1-bromo-2-propanol + 2-bromo-1-propanol (90:10) | (1.5) |
| 7 | Propylene | KBr | CP | (10) | 4.5 | 1-bromo-2-propanol + 2-bromo-1-propanol (90:10) | (0.5) |
| 8 | Propylene | KBr | LP | (50) | 6 | 1-bromo-2-propanol + 2-bromo-1-propanol (90:10) | (1.0) |
| 9 | Propylene | KBr | SWP[1] | (1) | 6 | 1-bromo-2-propanol + 2-bromo-1-propanol (90:10) | (0.2) |
| 10 | Propylene | KBr | SWP[2] | (1) | 6 | 1-bromo-2-propanol + 2-bromo-1-propanol (90:10) | (0.03) |
| 11 | Propylene | KI | CP | (10) | 3 | 1-iodo-2-propanol + 2-iodo-1-propanol (90:10) | (1.5) |
| 12 | Propylene | KI | HRP | (5) | 6 | 1-iodo-2-propanol + 2-iodo-1-propanol (90:10) | (0.3) |
| 13 | Butene-1 | KBr | CP | (10) | 3 | 1-bromo-2-butanol + 2-bromo-1-butanol | (0.5) |
| 14 | Isobutylene | KBr | CP | (10) | 3 | 1-bromo-2-methyl-2-propanol | (0.5) |
| 15 | cis-Butene-2 | KBr | CP | (10) | 3 | 3-bromo-2-butanol | |
| 16 | trans-Butene-2 | KBr | CP | (10) | 3 | 3-bromo-2-butanol | (0.6) |
| 17 | Allene | KBr | CP | (10) | 3 | 2-bromo-2-propen-1-ol | (0.4) |
| 18 | 1,3-Butadiene | KBr | CP | (10) | 3 | 1-bromo-3-buten-2-ol + 2-bromo-3-buten-1-ol + 1,4-dibromo-2,3-butanediol (98:1:1) | (2.6) |

2 monochlorodimedon units/ml.

Horseradish Peroxidase (HRP). Purchased from Sigma Chemical Company (Catalogue #P-8250).

The halohydrins are identified by gas chromatography/mass spectrometry. The halohydrin and its corresponding epoxide (after treatment of the halohydrin with base) are compared with authentic samples. The analysis of propylene bromohydrin illustrates the procedure:

10 μl of the reaction mixture was injected into a Perkin Elmer Model 3920 gas chromatograph, equipped with a 6 foot by ⅛ inch coiled, stainless steel column, packed with Porapak R (80/100 mesh) and attached to a Dupont Model 21-491 mass spectrometer operating at 70 eV ionization. Flow rate was set at 30 ml/minute for helium and the column temperature was programmed for 185° C. to 220° C. at a rate of 1° C./minute. Retention times for the propylene bromohydrins were 9 minutes for 1-bromo-2-propanol and 10 minutes for 2-bromo-1-propanol.

Product identity was confirmed by comparison with authentic samples of propylene bromohydrin: 1-bromo-2-propanol was purchased from Pfaltz and Bauer, Inc.; 2-bromo-1-propanol was synthesized by lithium aluminum hydride reduction of 1-bromopropionyl chloride. The reaction products and the authentic samples showed the same retention times and identical mass spectra: bromine was identified by the presence of the M and M+2 isotope clusters of equal intensity; the molecular ion for both isomers was confirmed by chemical ionization with isobutane reagent gas (M+; m/e 138+140); for 1-bromo-2-propanol the major fragmentation was the expected loss of $CH_2Br$ while for 2-bromo-1-propanol the major fragmentation was the expected loss of $CH_3CHBr$.

Further, both bromohydrins were converted to propylene epoxide by addition of 10% sodium hydroxide to their aqueous solutions to yield a pH greater than 10. Identity of propylene epoxide was confirmed by gas chromatography/mass spectrometry comparison with an authentic sample (purchased from Aldrich Chemical Company, Inc.). The reaction product after base treatment and the authentic sample showed the same reten-

EXAMPLES 19–31

Liquid or Solid Olefins

Dilute hydrogen peroxide (1 mg/ml final), potassium bromide (10 mg/ml final), liquid or solid olefin (5 mg/ml final) and 0.1 M potassium phosphate buffer (pH 3) are mixed together in a 100 milliliter Pyrex flask at room temperature and room pressure. Chloroperoxidase (10 units; prepared as in Examples 1–18) is added. Sample is withdrawn at 30 minutes and analyzed for halohydrin.

The halohydrins are identified by gas chromatography/mass spectroscopy. The halohydrin and its corresponding epoxide (after treatment of the halohydrin with base) are compared with authentic samples. The analysis of allyl bromide bromohydrin (Example 27) illustrates the procedure:

10 μl of the reaction mixture was injected into a Perkin Elmer Model 3920 gas chromatograph, equipped with a 6 foot by ⅛ inch coiled, stainless steel column, packed with 3% OV225 on GAS-CHROM Q (100/120 mesh), and attached to a Dupont Model 21-491 mass spectrometer operating at 70 eV ionization. Flow rate was set at 30 ml/minute for helium and the column temperature was programmed from 140° C. to 200° at a rate of 2° C./minute. Retention times for the allyl bromide bromohydrins were 17 minutes for 1,3-dibromo-2-propanol and 20 minutes for 2,3-dibromo-1-propanol.

Product identity was confirmed by comparison with authentic samples of the bromohydrins. (Both were purchased from Aldrich Chemical Company, Inc.). The reaction products and the authentic samples showed the same retention times and identical mass spectra: 2 bromines per molecule were identified by the presence of the M, M+2 and M+4 isotope clusters of 1:2:1 intensity; the molecular ion for both isomers was visible (M+; m/e 216+218+220); for 1,3-dibromo-2-propanol the major fragmentation was the expected loss of $CH_2Br$ while for 2,3-dibromo-1-propanol the major fragmentation was the expected loss of $CH_2BrCH_2Br$.

Further, both bromohydrins were converted to epibromohydrin (i.e. the epoxide of allyl bromide bromohydrin) by addition of 10% sodium hydroxide to their aqueous solutions to yield a pH>10. Identity of epibromohydrin was confirmed by gas chromatography/mass spectrometry comparison with an authentic sample (purchased from Aldrich Chemical Company, Inc.). The reaction product after base treatment and the authentic sample showed the same retention time (5 minutes) and identical mass spectra (M+; m/e 136+138).

Results are set forth in Table II.

TABLE II

| | | Bromohydrin Product | |
|---|---|---|---|
| Ex. | Olefin | MAJOR PRODUCT | MINOR PRODUCT |
| 19 | Pentene-1 | 1-Bromo-2-pentanol | 2-Bromo-1-pentanol |
| 20 | 2-Methyl-Butene-2 | 3-Bromo-2-methyl-2-butanol | 2-Bromo-2-methyl-3-butanol |
| 21 | Isoprene | 1-Bromo-2-methyl-3-buten-2-ol | 2-Bromo-2-methyl-3-buten-1-ol + 1-Bromo-3-methyl-3-buten-2-ol |
| 22 | 1,4-Pentadiene | 1-Bromo-4-penten-2-ol | 2-Bromo-4-penten-1-ol |
| 23 | Octene-1 | 1-Bromo-2-octanol | 2-Bromo-1-octanol |
| 24 | Decene-1 | 1-Bromo-2-decanol | 2-Bromo-1-decanol |
| 25 | Dodecene-1 | 1-Bromo-2-dodecanol | 2-Bromo-1-dodecanol |
| 26 | 1-Bromo-3-buten-2-ol | 1,4-Dibromo-2,3-butanediol | |
| 27 | Allyl bromide | 1,3-Dibromo-2-propanol | 2,3-Dibromo-1-propanol |
| 28 | Allyl alcohol | 1-Bromo-2,3-propanediol | 2-Bromo-1,3-propanediol |
| 29 | Allyl chloride | 1-Bromo-3-chloro-2-propanol | 2-Bromo-1-chloro-3-propanol |
| 30 | 1,7-Octadiene | 1-Bromo-7-octen-2-ol | 1,8-Dibromo-2,7-octanediol |
| 31 | Styrene | (2-Bromo-1-hydroxyethyl)-benzene | (1-Bromo-2-hydroxyethyl)-benzene |

EXAMPLE 32

The procedure of Examples 2 and 6 are followed substituting a mixed ethylenepropylene stream for the single olefin.

The result is 1.4 mg/ml of 2-bromoethanol and 0.9 mg/ml of 1-bromo-2-propanol+2-bromo-1-propanol (90:10).

EXAMPLE 33

The importance of immobilizing the halogenating enzyme and using a slow feed of $H_2O_2$ by in situ enzymatic generation are shown in this example. Halide salt (10 mg/ml final) and 0.1 M potassium phosphate buffer (pH 6) are mixed together in four 100 milliliter Pyrex flasks at room temperature and room pressure. Propylene is bubbled into the reaction mixtures. Sample is withdrawn at 60 minutes and analyzed for halohydrin. The variable conditions and the results are set forth in Table III. These results indicate that the use of immobilized halogenating enzyme coupled with a slow feed (slow to the point of use as generated) of $H_2O_2$ greatly improves the production of propylene bromohydrins, from which propylene oxide is easily obtained.

TABLE III

| Reaction | $H_2O_2$ Feed | Lactoperoxidase | Propylene Bromohydrin Yield mg/ml |
|---|---|---|---|
| 1 | Direct addition (1) | Non-immobilized (3) | .008 |
| 2 | Direct addition (1) | Immobilized (4) | .03 |
| 3 | In situ generation (2) | Non-immobilized (3) | .21 |
| 4 | In situ generation (2) | Immobilized (4) | 1.51 |

Footnotes:
(1) 1 mg/ml $H_2O_2$ final
(2) 0.2 ml of 1.0M a-D-glucose and 0.1 ml of glucose oxidase (Sigma Chemical Corp., Catalogue #G-6500) per 10 ml of reaction mixture.
(3) from P.L. Biochemicals, Inc., 20 units added.
(4) from P.L. Biochemicals, Inc., bound to Sepharose, 20 units added.

EXAMPLE 34

The use of immobilized seaweed peroxidase is shown in this example.

The immobilized seaweed peroxidase is prepared as follows:

Glass beads (obtained from Sigma Chemical Company, PG-700-200) are activated by suspending 1 g of glass beads in 18 ml of deionized water. 2 ml of 10% (v/v α-aminopropyltriethyoxyl silane are added and the pH of the mixture is adjusted to 3–5 with 6 N HCl. The mixture is shaken at 75° C. for 2 hours. The glass beads are then vacuum dried overnight at 80° C. 3.2 ml of purified Coralina sp. enzyme, prepared as in Examples 1–18, and 50 mg. of water soluble carbodiimide are added to the glass beads. The pH is adjusted to 4.5, and the mixture is then shaken at 4° C. overnight. The product—enzyme coated beads—is washed with water. The activity is measured as 2 monochlorodimedon units/g of beads.

A reaction using 1 g of the seaweed peroxidase coated glass beads is run as in Example 33, reaction 4, with these modifications.

(a) 40 mg/ml KBr final
(b) 50 mg/ml α,D-glucose
(c) 1.0 ml of glucose oxidase

The result is:

| Reaction time, hour | Propylene Bromohydrin (mg/ml) |
|---|---|
| 4 | 9.0 |
| 8 | 13.3 |
| 10 | 16.5 |
| 21 | 24.1 |

EXAMPLE 35

The procedure of Example 34 is followed substituting KI for KBr.

The result is 3.0 mg/ml of propylene iodohydrin at 1 hour.

EXAMPLE 36

The use of cells of *Hansenula polymorpha* ATCC 26012 as a source of methanol oxidase to generate $H_2O_2$ is shown in this example.

Cells of the microorganism are prepared as follows:

The culture is maintained on agar slants at 37°, with periodic transfer. The composition of the agar medium per liter is $NaNO_3$ (3 g), KCl (0.5 g), $MgSO_4.7H_2O$ (0.5 g), acidified 1% $FeSO_4.7H_2O$ (1 ml), $KH_2PO_4$ (1 g), glucose (40 g), NaCl (32.14 g), yeast extract (2 g), and agar (15 g). pH is adjusted to 6.0 with 10% NaOH prior to sterilization under standard conditions. Growth of the culture to be used as a source of methanol oxidase activity is carried out on a medium of the following composition per liter: $(NH_4)_2HPO_4$ (6 g), $MgSO_4.7H_2O$ (2 g), and yeast extract (5 g). pH is adjusted to 5.0 with 85% $H_3PO_4$ prior to sterilization under standard conditions. Fermentations are run in 125 ml Erlenmeyer flasks containing 20 ml of this medium to which 0.1 ml sterile methanol is added. The fermentations are performed at 37°, 200 rpm on a New Brunswick shaker, 2"-throw, for 1-3 days. The cells are harvested by centrifugation, washed once with 0.1 M phosphate buffer and then resuspended at 1/5 the original fermentation volume in 0.1 M phosphate buffer, pH 6.0. The cells are stored in the refrigerator at 4° C. for up to one week without substantial loss of activity.

A reaction with lactoperoxidase is run as in Example 33, reaction 3 with these modifications:
(a) 0.1 ml 3% methanol instead of 0.1 ml 1 M α-D-glucose.
(b) 1 ml of above-described suspension of cells of Hansenula polymorpha ATCC instead of 0.1 ml glucose oxidase.

The reaction mixture is analyzed for propylene bromohydrins after 60 minutes. The total yield is 175 μg/ml.

EXAMPLE 37

The ability to convert propylene to propylene epoxide, enzymatically, without isolation of the intermediate halohydrin is shown in this Example. Flavobacterium sp. (Cetus #5095) contains a halohydrin epoxidase, which converts halohydrins to epoxides.

The microorganism is grown at 25°, 200 rpm 2"-throw on a New Brunswick shaker in a medium reported in the literature (C. E. Castro and E. W. Bartnicki, Biochemistry 7:3213 (1968)). 100 ml of medium is used per 500 ml Erlenmeyer flask. The microorganism is maintained on slants using an agarized version of the liquid medium. The seed stage is usually 48 hours. The cells for use in the conversion reaction are then grown for an additional 2-3 days, using a 1-5% inoculum from the seed stage.

A washed cell preparation of the microorganism is prepared by standard procedures and is finally resuspended at a twenty-fold concentration (as compared to the concentration in the growth stage flasks) in the appropriate phosphate buffer. Dry weight of cells in these washed cell suspensions is 15 mg/ml.

The procedure of Example 8 is followed, with the addition of 30 mg of Flavobacterium sp. cells to the reaction mixture.

The results obtained are 0.2 mg/ml propylene bromohydrin and 0.3 mg/ml propylene epoxide.

EXAMPLE 38

The procedure of Example 37 is followed except ethylene is substituted for propylene and chloroperoxidase (2 units) is substituted for lactoperoxidase.

The results obtained are 100 μg/ml ethylene bromohydrin and 5 μg/ml ethylene epoxide.

EXAMPLE 39

The ability to produce oxide from propylene in an integrated immobilized enzyme/cell system in a continuous-flow column configuration is demonstrated in this example. The general conversion proceeds in the following manner:

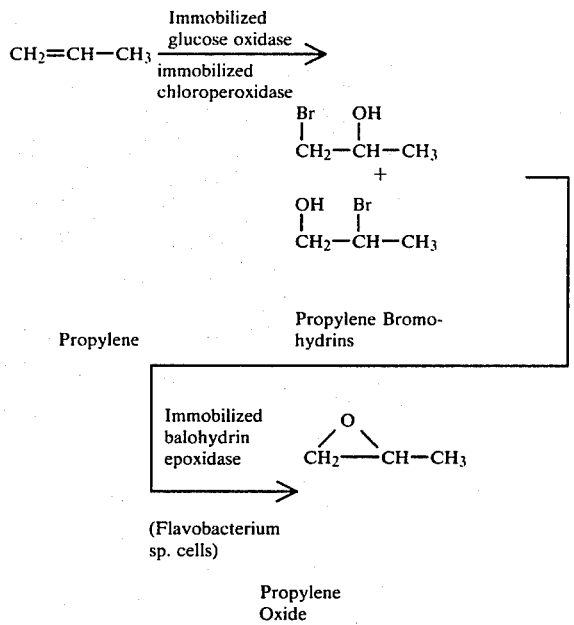

By way of example, the glucose oxidase can be covalently immobilized with AH-Sepharose 4B; the chloroperoxidase can be ionically immobilized on DEAE-sephadex A50 beads, and the halohydrin epoxidase can be insolubilized inside the cells with polyacrylamide gel.

By way of example, one column configuration includes a first region which contains the initial mixture (50 ml) of reaction components: propylene gas continuously bubbled in, 0.42 M KBr, 0.01 M glucose, and phosphate buffer (pH 4.4, 0.3 M). The mixture is slowly dripped onto a column of immobilized chloroperoxidase (CP) and glucose oxidase (GO) prepared by mixing 5 ml CP-beads and 1 ml GO-beads. This is the first stage of the system to produce propylene bromohydrin.

The details of immobilizing glucose oxidase and chloroperoxidase follow:

The glucose oxidase (1460 units/ml) is purchased from Sigma Chemical Company. The insoluble beads of AH-Sepharose 4B are obtained from Pharmacia Fine Chemical Company. Both enzyme and beads are adjusted to pH 5.0. To immobilize the enzyme onto the beads, 10 ml glucose oxidase and 10 ml beads are mixed. The coupling reaction is initiated by the addition of 2 ml N-cyclohexyl-N'(2-(4-methyl-morpholino)-ethyl)-carbodiimide solution (100 mg/2 ml). The reaction mixture is incubated at 4° C. overnight. The beads are then washed with 0.03 M phosphate buffer (pH 4.4). The glucose oxidase-AH-Sepharose 4B beads are stored at 4° C. for use.

The chloroperoxidase (prepared as in Examples 1-18) is immobilized by mixing equal volume dialyzed chloroperoxidase with hydrated DEAE-Sephadex A50 beads. The enzyme-beads complex are washed three times with 0.03 M phosphate buffer (pH 4.4). The activity of the beads is estimated to be 2.17 units/ml with monochlorodimedon assay. The immobilized chloroperoxidase is stored at 4° C. for future use.

The resulting eluate, containing excess reagents as well as propylene bromohydrin and gluconic acid, is adjusted to pH 6 with phosphate buffer (pH 6, 1.0 M) to allow for substantial activity with halohydrin epoxidase contained in the next column region. The immobilization of halohydrin epoxidase is performed by immobilizing the intact cells of Flavobacterium sp. (prepared as in Example 37) with the following reaction mixture:

Flavobacterium sp.: 4 gm (wet weight)
Saline Solution: 4 ml
Acrylamide monomer: 750 mg
Bis-acrylamide: 40 mg
TEMED: 25 λ
Ammonium persulfate: 0.5 ml (2.5%)

The polymerized gel is then blended into beads with a Waring blender (low speed, 20 seconds). This is the second stage of the system, producing propylene oxide from the propylene bromohydrins of the first stage.

The results obtained are 75 μg/ml propylene bromohydrin and 5 μg/ml propylene epoxide at a flow rate through the column of 1 ml/hour.

The foregoing description and accompanying examples therefore demonstrate that epoxides and glycols may be produced from alkenes at room temperature. The process requires essentially no energy additions and is applicable to a wide variety of substrates including gaseous alkenes such as ethylene and propylene. Various modifications of the invention will become apparent to those skilled in the art from the foregoing description. Such modifications are intended to fall within the scope of the following claims.

What we claim is:

1. A method for the manufacture of epoxides or glycols from olefins comprising, providing a reaction mixture of a halogenating enzyme, an oxidizing agent and a halide ion source in a reaction vessel, introducing an olefin into said reaction vessel and maintaining said olefin in contact with said reaction mixture for a sufficient period of time to convert said olefin to a halohydrin, and converting said halohydrin to an epoxide or glycol.

2. A method in accordance with claim 1 wherein said halogenating enzyme is a perioxidase derived from a member selected from the group consisting of the micoroorganism Caldariomyces fumago, seaweed, milk, thyroid, leukocytes and horseradish.

3. A method in accordance with claim 1 wherein said halogenating enzyme is a peroxidase derived from a member selected from the group consisting of the microorganism Caldariomyces fumago, seaweed and milk.

4. A method in accordance with claim 1 wherein said oxidizing agent is hydrogen peroxide.

5. A method in accordance with claim 1 wherein said halide ion source is a water soluble halide salt.

6. A method in accordance with claim 1 wherein the reaction is conducted with the pH range of from about 2.2 to about 8.0.

7. A method in accordance with claim 4 wherein said hydrogen peroxide is present during said reaction at a molar ratio of from about 0.5:1 to about 50:1 with respect to said olefin.

8. A method in accordance with claim 4 wherein said hydrogen peroxide is generated in situ.

9. A method according to claim 1 wherein said oxidizing agent is hydrogen peroxide generated in situ by means of glucose-2-oxidase on a glucose substrate with co-production of D-arabino-2-hexosulose, and wherein the D-arabino-2-hexosulose is converted to D-fructose to provide the latter as a by-product to the epoxide or glycol.

10. A method according to claim 1 wherein said oxidizing agent is hydrogen peroxide generated in situ by means of methanol oxidase on a methanol substrate with co-production of formaldehyde.

11. A method according to claim 1 wherein said oxidizing agent is hydrogen peroxide generated in situ by means of glucose oxidase on a glucose substrate with co-production of gluconic acid.

12. A method in accordance with claim 1 wherein said halogenating enzyme is derived from a member selected from the group consisting of the microorganism Caldariomyces fumago, lactoperoxidase, and seaweed, said oxidizing agent is hydrogen peroxide, said halide ion source is selected from the group consisting of the chloride, bromide and iodide salts of sodium and potassium, and said reaction takes place in an aqueous environment at ambient conditions of temperature and pressure.

13. A method in accordance with claim 1 wherein said halohydrin is converted to an epoxide by reaction with aqueous slaked lime.

14. A method in accordance with claim 12 wherein said epoxide is converted by hydration to a glycol.

15. A method in accordance with claim 1 wherein said halohydrin is converted to an epoxide enzymatically by means of a halohydrin epoxidase.

16. A method in accordance with claim 15 wherein said halohydrin epoxidase is produced by an organism selected from the group consisting of a bacterium of the species Flavobacterium, the fungus Caldariomyces fumago, and the seaweed Laurencia pacifica.

17. A method in accordance with claim 15 wherein said halohydrin is enzymatically converted to an epoxide in the same reactor in which said halohydrin is formed.

18. A method in accordance with claim 15 wherein said halogenating enzyme is immobilized by attachment to a carrier in a first zone of said reaction vessel, said epoxidase is immobilized by attachment to a carrier in a second zone in said reaction vessel, and said olefin is passed continuously through said reaction vessel to continuously provide an olefin epoxide product.

19. A method in accordance with claim 15 wherein said halogenating enzyme is immobilized by attachment to a carrier in a first zone of said reaction vessel, said epoxidase is immobilized by attachment to a carrier in a second zone in said reaction vessel, wherein said oxidizing agent is hydrogen peroxide generated in situ by use of an enzyme which is immobilized by attachment to a carrier in said first zone of said reaction vessel, and wherein said olefin is passed continuously through said reaction vessel to continuously provide an olefin epoxide product.

20. A method in accordance with claim 1 wherein said olefin is selected from the group consisting of: ethylene, propylene, butene-1, pentene-1, octene-1, decene-1, dodecene-1, isobutylene, cis-butene-2, transbutene-2, 2-methyl-butene-2, 1,3-butadiene, 1,4-pentadiene, isoprene, and 1,7-octadiene.

21. A method in accordance with claim 1 wherein said olefin is selected from the group consisting of: styrene, allyl alcohol, allyl chloride, allyl bromide, and allene.

22. A method in accordance with claim 1 wherein said hydrogen peroxide is generated in situ by means of an enzyme, and wherein said halohydrin is converted to an epoxide by means of an enzyme.

23. In a method for the manufacture of epoxides or glycols from olefins wherein an intermediate halohydrin is provided which is converted to an epoxide or glycol, the step of producing the halohydrin from the olefin comprising, providing a reaction mixture of a halogenating enzyme, an oxidizing agent and a halide ion source in a reaction vessel, and introducing an olefin into said reaction vessel and maintaining said olefin in contact with said reaction mixture a sufficient period of time to convert said olefin to a halohydrin.

24. A method in accordance with claim 23 wherein said halogenating enzyme is a peroxidase derived from a member selected from the group consisting of the microorganism *Caldariomyces fumago*, seaweed, milk, thyroid, leukocytes, and horseradish.

25. A method in accordance with claim 24 wherein said halogenating enzyme is a peroxidase derived from a member selected from the group consisting of the microorganism *Caldariomyces fumago*, seaweed and milk.

26. A method in accordance with claim 25 wherein said oxidizing agent is hydrogen peroxide.

27. A method in accordance with claim 25 wherein said halide ion source is a water soluble halide salt.

28. A method according to claim 25 wherein said hydrogen perioxide is generated in situ by means of an enzyme at a rate such that the hydrogen peroxide is present during said reaction at a molar ratio which is about 1:1 or less with respect to said olefin.

29. A method according to claim 25 wherein said oxidizing agent is hydrogen peroxide generated in situ by means of glucose-2-oxidase on a glucose substrate with co-production of D-arabino-2-hexosulose, and wherein the D-arabino-2-hexosulose is converted to D-fructose.

30. In a method for the manufacture of epoxides or glycols from olefins by producing an intermediate halohydrin from the olefin by reaction with a halogenating enzyme, an oxidizing agent and a halide ion source, and by conversion of the halohydrin to an epoxide or glycol, the steps of generating hydrogen peroxide as the oxidizing agent in situ by reaction of glucose-2-oxidase on a glucose substrate to produce D-arabino-2-hexosulose as a co-product, and converting the D-arabino-2-hexosulose to D-fructose as a co-product to the epoxide or glycol.

31. A method in accordance with claim 30 wherein the D-arabino-2-hexosulose is converted to D-fructose by chemical hydrogenation.

* * * * *